(12) United States Patent
Whipple

(10) Patent No.: US 9,463,057 B2
(45) Date of Patent: Oct. 11, 2016

(54) ORTHOPEDIC FASTENER

(71) Applicant: Dale Whipple, Acworth, GA (US)

(72) Inventor: Dale Whipple, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 254 days.

(21) Appl. No.: 14/156,782

(22) Filed: Jan. 16, 2014

(65) Prior Publication Data
US 2015/0196335 A1 Jul. 16, 2015

(51) Int. Cl.
*A61B 17/86* (2006.01)
*A61B 17/70* (2006.01)
*F16B 35/04* (2006.01)
*F16B 25/00* (2006.01)

(52) U.S. Cl.
CPC ......... *A61B 17/8625* (2013.01); *A61B 17/863* (2013.01); *A61B 17/8635* (2013.01); *A61B 17/7037* (2013.01); *A61B 17/8605* (2013.01); *F16B 25/0052* (2013.01); *F16B 25/0057* (2013.01); *F16B 35/04* (2013.01)

(58) Field of Classification Search
CPC .................................................. A61B 17/863
See application file for complete search history.

(56) References Cited

U.S. PATENT DOCUMENTS

| | | | |
|---|---|---|---|
| 4,150,702 A * | 4/1979 | Holmes | F16B 39/30 411/310 |
| 5,601,553 A | 2/1997 | Trebing et al. | |
| 6,030,162 A | 2/2000 | Huebner | |
| 6,565,573 B1 | 5/2003 | Ferrante et al. | |
| 8,333,590 B2 | 12/2012 | Hansson | |
| 8,419,779 B2 | 4/2013 | Rinner | |
| 2002/0087161 A1* | 7/2002 | Randall | A61B 17/683 606/916 |
| 2011/0288598 A1* | 11/2011 | Moed | A61B 17/8625 606/303 |
| 2012/0136398 A1* | 5/2012 | Mobasser | A61B 17/8635 606/311 |
| 2012/0178048 A1 | 7/2012 | Cottrell | |
| 2013/0218213 A1 | 8/2013 | Lemoine | |
| 2014/0005728 A1* | 1/2014 | Koay | A61B 17/8057 606/281 |

FOREIGN PATENT DOCUMENTS

| | | | | |
|---|---|---|---|---|
| DE | WO 2013131974 A1 * | 9/2013 | | A61B 17/7291 |
| WO | 2013068088 | 5/2013 | | |

* cited by examiner

*Primary Examiner* — David Bates
*Assistant Examiner* — Olivia C Chang
(74) *Attorney, Agent, or Firm* — David L. King

(57) ABSTRACT

An orthopedic fastener (10) has a head (50) and a shank (20). The shank (20) extends from the head (50) to a distal tip (11). The shank (20) has a leading end (1) adjacent the distal tip (11) and a trailing end (3) adjacent the head (50). An intermediate transition (2) is positioned between the leading (1) and trailing ends (3). The leading end (1) has first threads (40) with one or more self-tapping cutting grooves (41) extending adjacent the distal tip (11) and through a plurality of the first threads (40). The trailing end (3) has a second thread (60) extending toward the head (50) from the intermediate transition (2). The intermediate transition (2) has one or more second cutting grooves (61) extending from at least a first thread (40) in the intermediate transition (2) through at least one of said second threads (60) to initiate tapping of the second threads (60) into cortical bone. The first and second cutting grooves (41, 61) in combination with the threads (40, 60) form threads in the bone to hold the fastener (10).

4 Claims, 3 Drawing Sheets

ID FASTENER

TECHNICAL FIELD

The present invention relates generally to bone fasteners, more particularly to an improved orthopedic fastener with an improved thread cutting feature to secure the fastener in bone.

BACKGROUND OF THE INVENTION

In orthopedic bone repair procedures, a variety of devices and implants have been devised to stabilize a bone fracture or to space vertebrae or attach ligaments or tendons to bone.

Most of these devices require the use of threaded fasteners or screws that are driven into the bone and held or anchored in place to the bone.

The bone structure typically has a hard outer surface or shell commonly referred to as cortical bone and a softer interior of a more open celled spongy structure of cancellous bone. Accordingly, the fastener must be held in place taking into account the structure of the bone.

A variety of unique thread configurations for bone screws have been developed for this purpose, the goal being to provide a safe and reliable fastening into the bone material.

The present invention provides a unique and advantageous design to create secure attachment of a bone fastener. Loosening of the fastener and damaging the threads cut into the bone are primary limitations of prior art fasteners.

These and other limitations in the prior art have been corrected and solved by the present invention as disclosed herein.

SUMMARY OF THE INVENTION

An orthopedic fastener has a head and a shank. The shank extends from the head to a distal tip. The shank has a leading end adjacent the distal tip and a trailing end adjacent the head. An intermediate transition is positioned between the leading and trailing ends. The leading end has a first thread with one or more self-tapping cutting grooves extending adjacent the distal tip and through a plurality of the first threads. The trailing end has a second thread extending toward the head from the intermediate transition. The intermediate transition has one or more cutting grooves. The intermediate transition has a second cutting groove extending from at least a first thread in the intermediate transition through at least one of said second threads to initiate tapping of the second threads into cortical bone. The first and second cutting grooves in combination with the threads form threads in the bone to hold the fastener.

The first thread has a pitch equal to said second thread. In one embodiment, the first thread has a pitch equal that of the second thread and the first thread extends between the distal end toward the head through the trailing end and the second thread extends helically spiraled between the first threads.

The orthopedic fastener wherein the self-tapping second cutting grooves allow the combination of the first and second threads in the trailing end to pass through first threads previously formed in the bone and the later cut second formed threads without damaging the bone threads and wherein a recess is positioned between the head and the end of the threads in the trailing end. The orthopedic fastener can be an implantable metal. The implantable metal can be one of titanium, stainless steel or cobalt chrome.

BRIEF DESCRIPTION OF THE DRAWINGS

The invention will be described by way of example and with reference to the accompanying drawings in which.

DETAILED DESCRIPTION OF THE INVENTION

Figure 1:
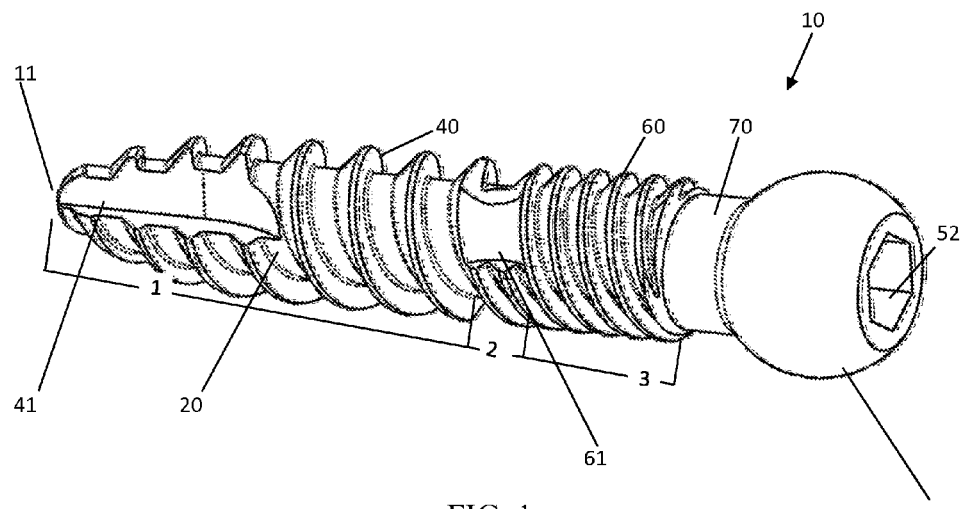
FIG. 1 is a perspective view of a bone screw or orthopedic fastener according to one embodiment of this invention.
Figure 2:
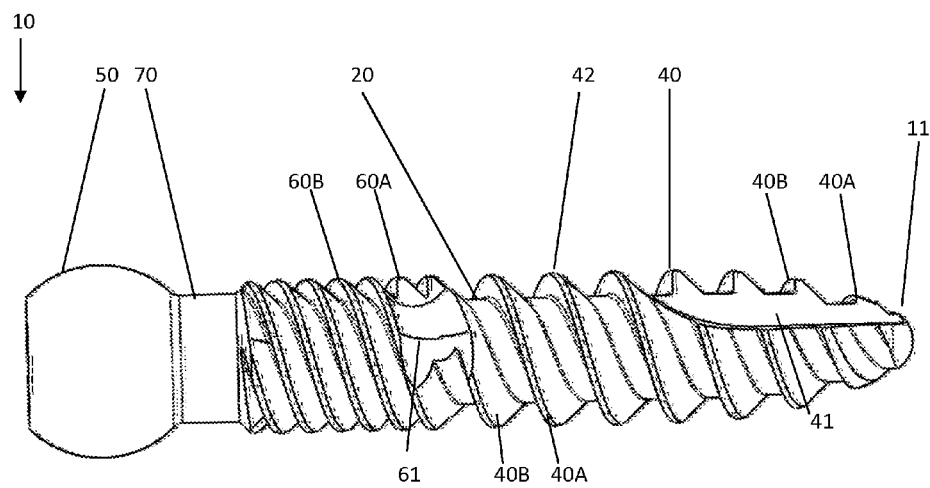
FIG. 2 is a side view of the fastener of FIG. 1.
Figure 3:
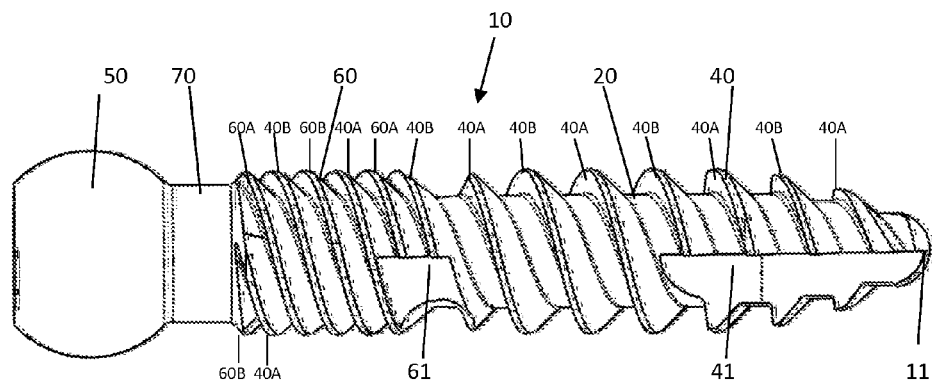
FIG. 3 is a top plan view of the fastener of FIG. 1.

Generally, an orthopedic fastener of this invention includes a head and a shank extending from the screw head to a distal tip. As used herein the term "head" means any head or top end of a fastener. The screw shank has trailing end including a recess adjacent to the head of the fastener, an intermediate section, and a leading end adjacent to the distal tip. The fastener also includes a substantially continuous thread along at least a portion of the shank which extends radially outward from the shank.

The fastener of this invention is adapted to be used alone or in conjunction with a system for use in repairing a bone fracture or in fixing an orthopedic implant in a patient. The fastener can be used alone to aid in the reduction of small bone fractures. Additionally, a fastener according to this invention can be used in conjunction with an orthopedic implant to fix the implant securely to the skeletal system of the patient.

FIGS. 1 through 5 depict one embodiment of a fastener 10 according to this invention. As shown in the figures, orthopedic fastener 10 includes a head 50 and a shank 20. Preferably, head 50 is adapted to contact the bone. The shank 20 extends from head 50 to a distal tip 11. A continuously extending first thread 40 extends evenly about the outer surface of the shank 20. The leading end adjacent distal tip 11 includes a fluted groove 41 for the removal of bone chips as the fastener 10 is implanted into the bone. Tip 11 of the fastener 10 is a self-tapping, non-self-drilling tip with a generally conical configuration with a foreshortened end, e.g. a frusto-conical tip.

Preferably, fastener 10 is a self-tapping, non-self-drilling bone screw so that tip 11 requires a predrilled hole before insertion into the bone and only first threads 40 of fastener 10 initially cut into the bone. The pitch of the threads 40 at tip 11 should be sufficiently small to advance the fastener 10 at a rate which allows tip 11 to advance into the bone, but sufficiently large to provide adequate bone purchase and to minimize the number of turns required to seat the fastener 10. A suitable pitch for threads 40 may be in the range of about 5 threads-per-inch to about 50 threads-per-inch.

In the preferred embodiment, the first threads 40 use a double start 40A, 40B thread with a high helix angle. Each is shown 180 degrees at the distal tip 11. At the trailing end 3 and the intermediate transition 2, the second threads 60 are also a double or two start thread 60A, 60B. This combination at the intermediate transition 2 initiates the additional two starts so the fastener 10 has four starts 40A, 40B and 60A, 60B as illustrated.

Each thread start preferably has one cutting groove. These cutting grooves are positioned at the beginning of each thread start. Accordingly, when there are two starts there are two cutting grooves spaced 180 degrees apart. This is as shown in the exemplary embodiment. Had three thread starts been employed, there would be three cutting grooves. In the present invention, the second set of threads has two starts so the fastener 10 has four cutting grooves, a first pair at the distal end and a second pair at the intermediate transition. In the illustrated embodiments, the second pair of cutting grooves are shown aligned with the first pair. This is a simple design preference since the two second thread starts could be at any location, the second pair of cutting grooves could be at any angle or location relative to the first pair. The important thing is each thread start within a pair in the present invention is 180 degrees apart. So the cutting grooves are 180 degrees apart in the transition 2 and similarly 180 degrees in the leading end 1 and, as shown, the intermediate grooves are aligned with the leading grooves along the shank. Alternatively, the starts and grooves relative to another section or end could be positioned at any angle relative to the other end or section. This is possible due to the second threads being started in a spaced location removed from the leading end 1 and distal tip 11 in the intermediate transition section 2.

The length of the fastener 10 should be adapted to correspond to the use. The fastener 10 can be any suitable length; preferably, the length of the fastener 10 is generally from about 20 mm to about 160 mm. More preferably, the length of fastener 10 is from about 30 mm to about 65 mm; preferably, the length of the shank 20 is approximately 4 to 6 mm less than the total length of the fastener, depending on the head shape and length.

Figure 4:
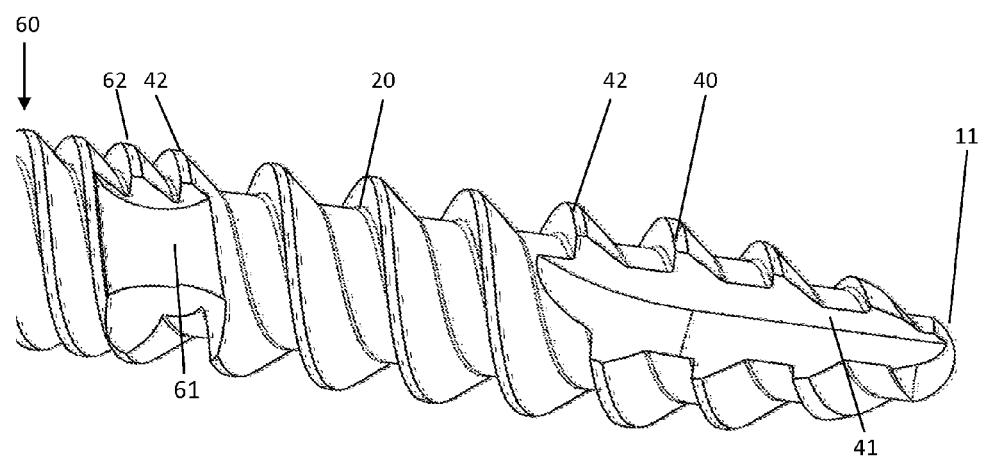
FIG. 4 is a partial perspective view of the fastener of FIG. 1.
Figure 5:
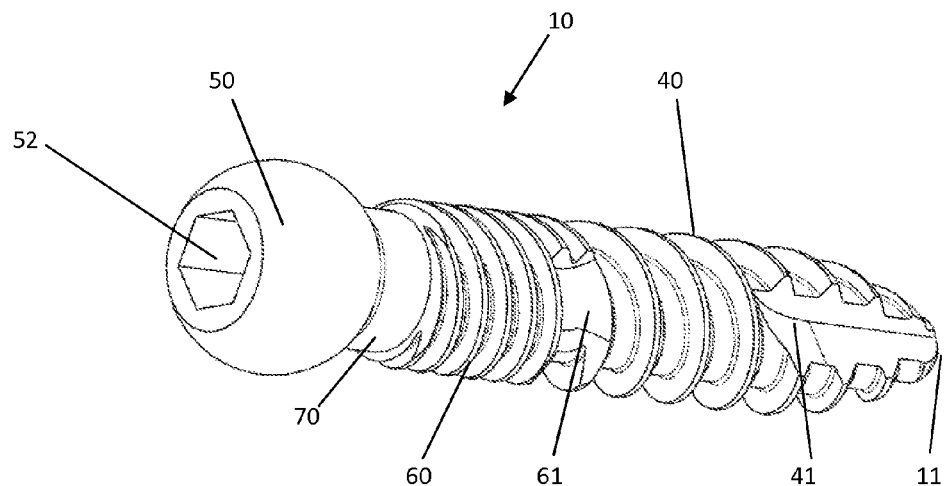
FIG. 5 is a perspective view of the head and internal surface of the fastener head of the fastener.

FIG. 4 is a side view of the fastener 10 of FIG. 1 and shows the detailed characteristics of the shank 20 and thread 40 of fastener 10. Shank 20 has a minor diameter and the first thread 40 a major diameter 42, defined by the diameter of the first thread 40. The thread height is equal to one half of the difference between the minor diameter and the major diameter 42. The difference is divided by two to account for the thread height on either side of the shank 20. Alternatively, the major diameter can be described as the sum of the minor shank diameter and twice the thread height. Note that shank minor diameter and thread major diameter and thread height can vary along the length of the fastener, as described below.

Shank 20 has three sections: trailing end 3; intermediate transition section 2; and leading end 1. Trailing end 3 is the portion of the shank 20 adjacent to head 50, leading end 1 is the portion of the shank 20 adjacent to the frusto-conical distal tip 11, and intermediate section 2 is the portion of the shank 20 between the leading and trailing ends. Each shank section has a minor shank diameter which may or may not remain constant from one section to another or within a section itself. Thus, trailing end has a first minor diameter, intermediate section as a second minor diameter, and leading end has a third minor diameter.

Intermediate section 2, of the embodiment shown in FIGS. 1-6, has a generally cylindrical geometry with a substantially constant minor diameter. The minor diameter can be any suitable length adapted to the size and function of the fastener. Preferably, the second minor diameter of the fastener 10 of the present invention is generally from about 6.0 mm to about 3.5 mm, more preferably from about 5.5 mm to about 4.0 mm, and most preferably from about 5.0 mm to about 4.5 mm.

In the embodiment shown, leading end 1 includes a taper or curvature extending from the end of the intermediate section 2 to the tip 11 at an angle theta θ or radius of curvature. Theta θ angle may also be any suitable angle, and is generally from about 1 degree to about 8 degrees, and preferably from about 1 degree to about 3 degrees. Thus, leading end 1 has a generally tapered geometry such that the minor diameter decreases from the section adjacent to intermediate section 2 in the direction of tip 11. The taper narrows towards the tip of the fastener 10 creating a frusto-conical tip area. The curvature has a radius or multiple radii to form a narrowing bullet like shape. This narrowing shape at the tip 11 end allows the fastener 10 to follow the pre-drilled hole more effectively and to advance more easily into the bone and through an aperture in an orthopedic implant.

Additionally, the first thread 40, thread height, and major diameter of a fastener 10 of this invention may vary along the length of the fastener body. As with the minor diameter, each shank section 1, 2 or 3 has a corresponding thread section and major diameter defined by the relative thread height.

First threads 40 extend in intermediate section 2 and have a substantially constant thread height due to the substantially constant second minor diameter of shank 20 and second major diameter in intermediate section 2. The major diameter of the thread is suited to the size of the fastener 10 and the intended function; preferably, the major diameter is from about 4.5 mm to about 8.5 mm, more preferably from about 5.5 mm to about 7.5 mm. Additionally, the ridge top of intermediate thread section can be relatively broad and wide as if the pointed end has been shaved off. This flat ridge top can be useful in the soft trabecular region of the bone where the leading end 1 and the intermediate section 2 will reside. The flat ridge top and constant minor diameter of the intermediate section also suit a fastener adapted for insertion through an aperture in an orthopedic implant for fixing the implant to the skeletal system of a patient.

Taper on leading end 1 results in a decreasing minor diameter, but the third major thread diameter is the same as second major thread diameter in the intermediate section 2 and trailing section 3. The substantially constant major diameter through intermediate section 2 and trailing end 3 results in a thread height of the threads along leading end 1 that is greater than the thread height of threads in intermediate section 2 and the trailing end 3. This increased thread height provides a better "bite" or grasp into the bone and more effectively draws the fastener 10 into the bone. The ridge top in this leading end 1 can be narrow, or pointy, for better pull through and purchase, particularly on the far cortex of the bone. The cortex, unlike the trabecula, is hard and provides strength to the bone, and thus requires a stronger grasp.

In trailing end 3 the thread heights 42, 62 of first and second threads 40, 60 are the same or slightly less than thread height 42 of the first threads 40 in the intermediate transition section 2 because both the minor shank diameter and the major thread diameter increase or stay the same along no taper or a slight taper in the direction of the head 50. A space is left between the threads and the head 50 providing room for a recess 70. This recess 70 can have an enlarged shank diameter for increased strength, and a tight wedge fit of the trailing end 3 of the fastener 10. The ridge top of threads 40, 60 along trailing end 3 is also generally narrow and pointy to provide for better seating of the fastener 10 and better purchase in the hard bone material of the near cortex.

The dual tapers, and an increased height of threads 40, 60 on the intermediate section 2 and trailing end 3 of fastener 10 provides improved purchase on both the near and far cortex of the bone. Intermediate section 2 with its second cutting groove 61 does not require a tapered geometry or a high thread height because it can lie in and occupy the inner portion of the bone with trabecular bone tissue, a softer, spongy bone tissue, and optionally occupies the interior of an aperture in an orthopedic implant when the fastener is used for fixing an orthopedic implant in a patient.

As discussed above, the trailing end 3 of shank 20 has an enlarged minor diameter to provide structural reinforcement for the recess 70 adjacent the head 50. In one embodiment of the invention, the head 50 includes a geometrically shaped socket 52 adapted to engage a corresponding driver and an axial bore extending from the bottom of the socket 52 into the upper portion of the fastener shank 20. The bore can include a connecting structure that corresponds to connecting structure on the driver. The connecting structure may be any suitable structure that couples the fastener to the driver, such as threads, or a snap ring. The orthopedic fastener can be an implantable metal. The implantable metal can be one of titanium, stainless steel or cobalt chrome.

Figure 6:
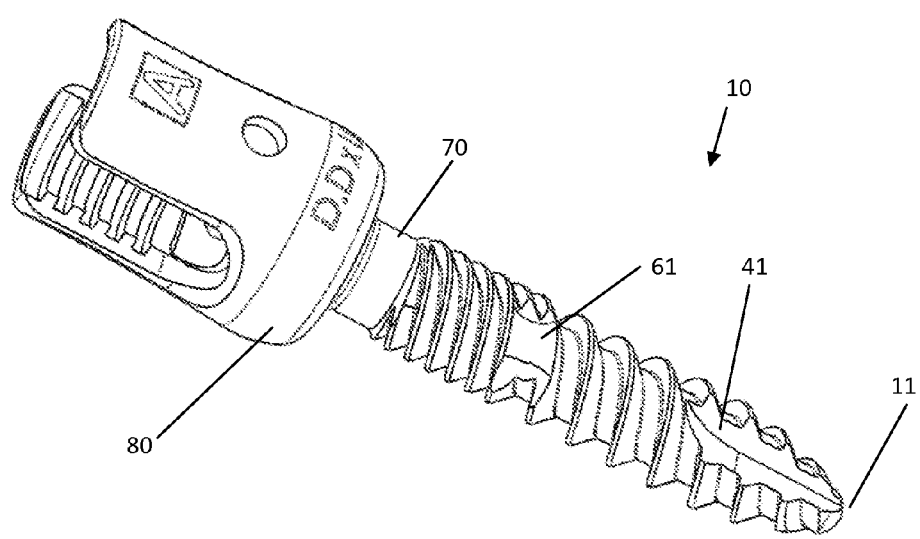
FIG. 6 is a view of the fastener of the present invention with a tulip attached.

As shown in FIG. 6, the fastener 10 can be used with a tulip 80.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An orthopedic fastener comprising:
a head; and a shank, the shank extending from the head to a distal tip, the shank having a leading end adjacent the distal tip and a trailing end adjacent a recess between the trailing end and the head and an intermediate transition section positioned between the leading and trailing ends;
wherein the shank has a first thread and a second thread, the first thread extending from the leading end to the trailing end and the second thread extending from the intermediate transition section to the trailing end, the first thread heaving one or more self-tapping cutting grooves extending adjacent the distal tip through a plurality of the first threads, and the intermediate transition section has one or more second self-tapping cutting grooves extending from at least one of the first threads in the intermediate transition section through at least one of said second threads to initiate tapping of the second threads into cortical bone, and wherein the first and second cutting grooves in combination with the threads are configured to form threads in the bone to hold the fastener, wherein the first thread has a pitch equal that of the second thread; and
wherein the second thread extends helically spiraled between the first thread in the intermediate transition section as the first thread and second thread extend to the trailing end from the intermediate transition section allowing the second threads to pass into the threads formed by the first thread as new second threads are being cut into the bone between the previously tapped first threads in the cortical bone, and wherein the shank exhibits an enlarged minor diameter in the trailing end as the first and second threads have a constant major diameter and a reduced thread height in the trailing end configured to form a tight wedge fit of the trailing end into the cortical bone.

2. An orthopedic fastener comprising:
a head; and a shank, the shank extending from the head to a distal tip, the shank having a leading end adjacent the distal tip and a trailing end adjacent a recess between the trailing end and the head and an intermediate transition section positioned between the leading and trailing ends;
wherein the shank has a first thread and a second thread, the first thread extending from the leading end to the trailing end and the second thread extending from the intermediate transition section to the trailing end, the first thread heaving one or more self-tapping cutting grooves extending adjacent the distal tip through a plurality of the first threads, and the intermediate transition section has one or more second self-tapping cutting grooves extending from at least one of the first threads in the intermediate transition section through at least one of said second threads to initiate tapping of the second threads into cortical bone, and wherein the first and second cutting grooves in combination with the threads are configured to form threads in the bone to hold the fastener, wherein the first thread has a pitch equal that of the second thread; and
wherein the second thread extends helically spiraled between the first thread in the intermediate transition section as the first thread and second thread extend to the trailing end from the intermediate transition section allowing the second threads to pass into the threads formed by the first thread as new second threads are being cut into the bone between the previously tapped first threads in the cortical bone, wherein the self-tapping second cutting groove allows the combination of the first and second threads in the trailing end to pass through the threads previously formed in the bone without damaging the bone threads as the shank exhibits an enlarged minor diameter in the trailing end as the first and second threads have a constant major diameter and a reduced thread height in the trailing end configured to form a tight wedge fit of the trailing end into the cortical bone.

3. The orthopedic fastener of claim 1 wherein the fastener is formed of an implantable metal.

4. The orthopedic fastener of claim 3 wherein the implantable metal is one of titanium, stainless steel or cobalt chrome.

* * * * *